United States Patent
Blatter et al.

(10) Patent No.: US 9,303,036 B2
(45) Date of Patent: Apr. 5, 2016

(54) CRYSTALLINE ASENAPINE HYDROCHLORIDE SALT FORMS

(75) Inventors: Fritz Blatter, Reinach (CH); Katharina Reichenbächer, Rheinfelden (DE)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 14/116,099

(22) PCT Filed: May 15, 2012

(86) PCT No.: PCT/EP2012/058962
§ 371 (c)(1),
(2), (4) Date: Jan. 10, 2014

(87) PCT Pub. No.: WO2012/156382
PCT Pub. Date: Nov. 22, 2012

(65) Prior Publication Data
US 2014/0121259 A1 May 1, 2014

(30) Foreign Application Priority Data
May 17, 2011 (EP) .................................... 11166310

(51) Int. Cl.
*C07D 491/04* (2006.01)
*C07D 491/044* (2006.01)

(52) U.S. Cl.
CPC .................................. *C07D 491/044* (2013.01)

(58) Field of Classification Search
CPC ..................................................... C07D 491/044
USPC ......................................................... 548/421
See application file for complete search history.

(56) References Cited

FOREIGN PATENT DOCUMENTS

WO    WO 2006/040314 A1    4/2006
WO    WO 2008/148515 A1    12/2008
WO    WO 2010/149727 A2    12/2010

OTHER PUBLICATIONS

Funke C. W., et al., "Physico-Chemical Properties and Stability of Trans-5-Chloro-2-Methyl-2, 3, 3A, 12B-Tetrahydro-1H-Dibenz-2,3:6,70 Oxepino-4,5-C) Pyrrolidine Maleate," Arzneimittel Forschung. Drug Research, ECV Editio Cantar Verlag, Aulendorf, DE, vol. 40, No. 5, May 1, 1990, pp. 536-539.
International Search Report, PCT/EP2012/058962 dated Jun. 18, 2012.

*Primary Examiner* — Shawquia Jackson
(74) *Attorney, Agent, or Firm* — Arent Fox LLP (57) ABSTRACT

Novel crystalline HCl salts of Asenapine, methods of their preparation and related pharmaceuticals and treatments are disclosed.

13 Claims, 2 Drawing Sheets

CRYSTALLINE ASENAPINE HYDROCHLORIDE SALT FORMS

CROSS-REFERENCE TO RELATED APPLICATION

This application is a National Stage entry of International Application No. PCT/EP2012/058962, filed May 15, 2012, which claims priority to European Application No. 11166310.0, filed May 17, 2011, the entire specifications, claims and drawings of which are incorporated herewith by reference.

FIELD OF THE INVENTION

The invention relates to novel crystalline HCl salts of Asenapine and to methods of their preparation. Furthermore the invention relates to the use of the novel salts in pharmaceutical compositions and the use of the novel salts as medicaments, preferably in the treatment of psychotic diseases or disorders such as schizophrenia and acute mania associated with bipolar disorder.

BACKGROUND PRIOR ART

Asenapine, trademark Saphris®, chemically trans-5-chloro-2-methyl-2,3,3a,12b-tetrahydro-1H-dibenz[2,3:6,7]oxepino[4,5-c]pyrrole, in sublingual dissolving tablet form, has been approved in US in August 2009 for the acute treatment of adult patients with schizophrenia and as monotherapy for acute mania or mixed episodes associated with bipolar disorders. The FDA has recently approved its use as ongoing maintenance treatment for schizophrenia and as adjunctive therapy with lithium or with valproate for bipolar 1 disorder.

Certain crystalline addition salts of Asenapine, for instance a fumarate (EP 0569096), salts with sulfonic acids (WO 98/54186), and a pamoate or hemipamoate salt (EP 0569096), are described in the literature. The pamoate salt is disclosed to be amorphous and the hemipamoate salt is a mixture of amorphous and crystalline phase, wherein the palmitate is described as oil. The marketed form is the maleate salt, which is disclosed to exist in polymorphic forms (WO 2006/106135). The known Asenapine salts have a low solubility in water. For example, Funke et. al. (Arzneim.-Forsch./Drug Res. 40, 1999, 536-539) reports that a saturated solution of the maleate salt of Asenapine at 23° C. has a concentration of 5.8 mg/ml at pH=4.4 (see also US2008/0306133 A1 regarding the solubility of Asenapine. This translates into a free base solubility of about 4.1 mg/ml, this value is in good agreement with solubility tests that were carried out with Asenapine maleate. WO 2009/135091 also discloses Asenapine and related compounds and salts thereof for treating a neuronal or non-neuronal indication. Peter van Hoof et al. (Amorphous Pharmaceutical Materials, September 2009) describe a method for validation of a drug product of Asenapine in solid state form.

The discovery of new crystalline salts of a pharmaceutically useful compound provides a new opportunity to improve the performance characteristics of a pharmaceutical product. It enlarges the repertoire of materials that a formulation scientist has available for designing, for example a pharmaceutical dosage form of a drug with targeted release profile or other desired characteristic.

For example, the premise for a sublingual dissolving tablet form is an active ingredient exhibiting good solubility in a fast dissolving matrix.

It is an objective of the invention to provide a pharmaceutically acceptable forms of Asenapine with good solubility.

It is also an object of the invention to provide a form of Asenapine having a good chemical and/or physical stability and/or good processability, both during its preparation and in the preparation of pharmaceutical compositions containing Asenapine.

The problems underlying the invention are solved by the subject matters defined in the claims.

Surprisingly, it was found that crystalline HCl salts of Asenapine as described below may provide beneficial properties e.g. regarding solubility and may furthermore enhance the performance of dosage forms comprising said Asenapine salts. In particular, using hydrochloric acid for preparing Asenapine salts allows providing crystalline salts that may have enhanced properties.

It has additionally, been found in the context of the invention that Asenapine HCl hydrates can be prepared by treating Asenapine HCl salts in anhydrous form with water. Likewise, it is possible to convert Asenapine HCl hydrates into Asenapine HCl anhydrous forms.

SUMMARY OF THE INVENTION

The invention thus provides the following (1) A crystalline salt, preferably a hydrate, further preferred a dihydrate, of trans-5-chloro-2-methyl-2,3,3a,12b-tetrahydro-1H-dibenz[2,3:6,7]oxepino[4,5-c]pyrrole (Asenapine) with hydrochloric acid (HCl).

(2) The crystalline salt of item 1 having a solubility in water of at least 15 mg/ml, preferably of at least 20 mg/ml, even more preferred of at least 24 mg/ml, calculated as free base equivalent and/or wherein the molar ratio of Asenapine to HCl in said salt is between 1:1.3 to 1.3:1.

(3) The crystalline salt of item 1 or 2, which comprises or consists of one or more, preferably one, selected from the group consisting of: (i) Asenapine HCl dihydrate, (ii) Asenapine HCl anhydrous form I, and (iii) Asenapine HCl anhydrous form II, wherein (i) Asenapine HCl dihydrate is characterized by X-ray powder diffraction reflections (Cu Kα radiation) comprising peaks at about 18.8°±0.2°, 9.3°±0.2°, 14.0°±0.2°, 24.9°±0.2° and 4.6±0.2° degrees two-theta, (ii) Asenapine HCl anhydrous form I is characterized by X-ray powder diffraction reflections (Cu Kα radiation) comprising peaks at about 25.1°±0.2°, 24.3°±0.2°, 9.0°±0.2°, 8.3°±0.2° and 18.0°±0.2° degrees two-theta, and/or (iii) Asenapine HCl anhydrous form II is characterized by X-ray powder diffraction reflections (Cu Kα radiation) comprising peaks at about 9.4°±0.2°, 24.8°±0.2°, 17.5°±0.2°, 18.9°±0.2° and 17.1°±0.2° degrees two-theta, when measured with Cu-Kα radiation.

In one preferred embodiment, the present invention is directed to Asenapine HCl dihydrate being characterized by X-ray powder diffraction reflections (Cu Kα radiation) comprising peaks at about 18.8°±0.2°, 9.3°±0.2°, 14.0°±0.2°, 24.9°±0.2° and 4.6°±0.2° degrees two-theta.

In another preferred embodiment, the present invention is directed to Asenapine HCl anhydrous form I being characterized by X-ray powder diffraction reflections (Cu Kα radiation) comprising peaks at about 25.1°±0.2°, 24.3°±0.2°, 9.0°±0.2°, 8.3°±0.2° and 18.0°±0.2° degrees two-theta.

In a further preferred embodiment, the present invention is directed to Asenapine HCl anhydrous form II being characterized by X-ray powder diffraction reflections (Cu Kα radiation) comprising peaks at about 9.4°±0.2°, 24.8°±0.2°, 17.5°±0.2°, 18.9°±0.2° and 17.1°±0.2° degrees two-theta.

Figure 1:
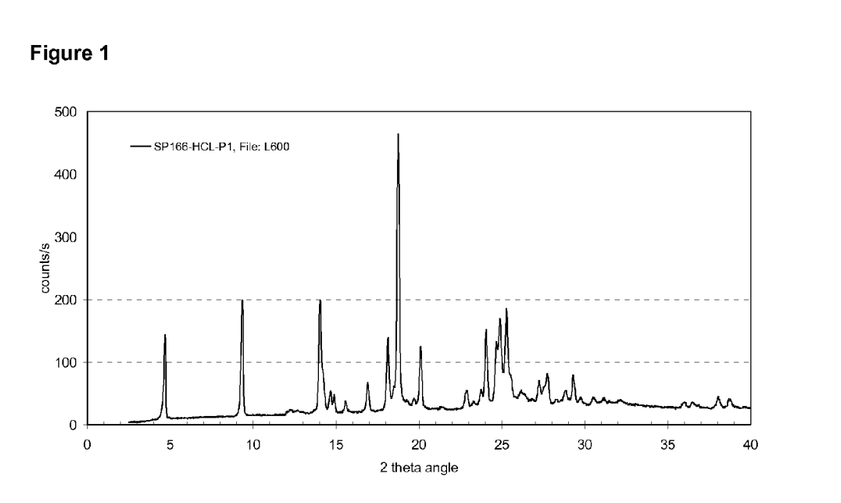
FIG. 1: X-ray powder diffraction pattern of Asenapine HCl dihydrate.

The crystalline Asenapine hydrochloride dihydrate is preferably characterized by a PXRD pattern substantially in accordance with FIG. 1, in particular the PXRD pattern comprises the peaks as given in Table 1.

Figure 2:
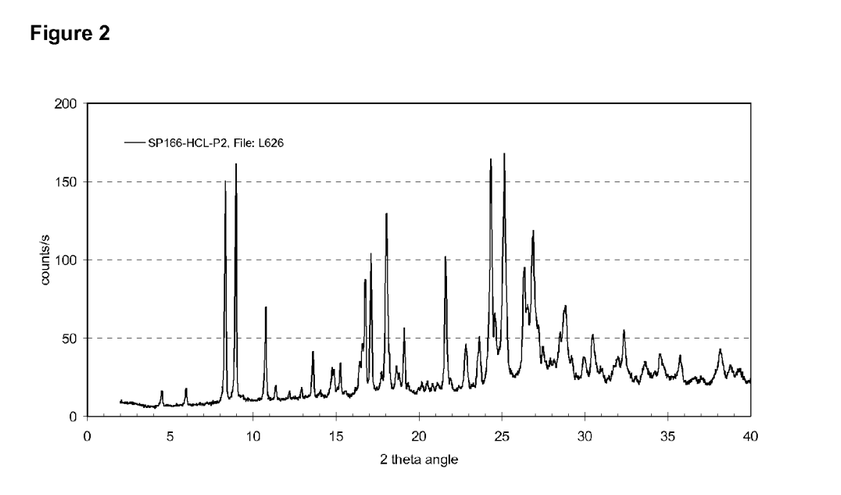
FIG. 2: X-ray powder diffraction pattern of Asenapine HCl anhydrous form I.

The crystalline Asenapine hydrochloride anhydrous form I is preferably characterized by a PXRD pattern substantially in accordance with FIG. 2, in particular the PXRD pattern comprises the peaks as given in Table 3.

Figure 3:
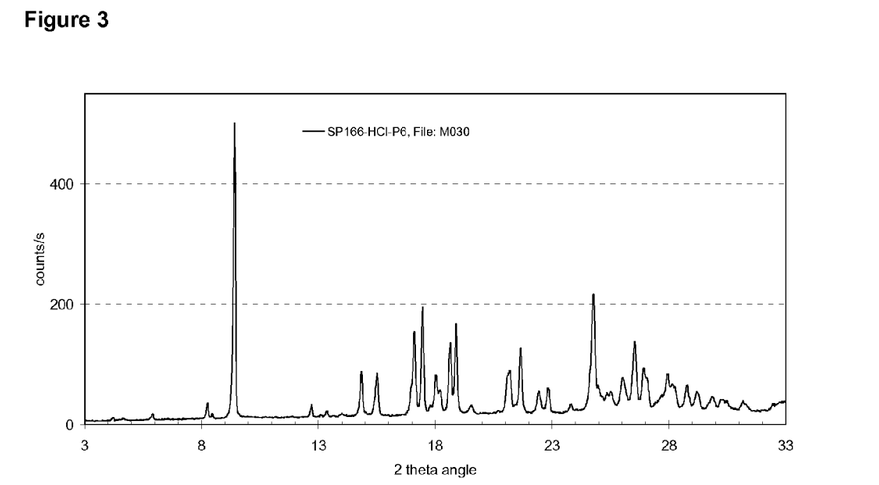
FIG. 3: X-ray powder diffraction pattern of Asenapine HCl anhydrous form II.

The crystalline Asenapine hydrochloride anhydrous form II is preferably characterized by a PXRD pattern substantially in accordance with FIG. 3, in particular the PXRD pattern comprises the peaks as given in Table 4.

In general, the Asenapine hydrochloride salt forms described herein are preferably characterized by their PXRD pattern, i.e. the peaks as given in the respective peak tables. Particularly suitable for characterizing the salts are the peaks having an intensity of vs (very strong), s (strong) and m (medium).

Preferably, the crystalline salt comprises at least 80 wt. %, further preferred at least 90 wt. %, even further preferred at least 95 wt. %, of one or more, preferably one, selected from the group consisting of, (i) Asenapine HCl dihydrate, (ii) Asenapine HCl anhydrous form I, and (iii) Asenapine HCl anhydrous form II.

(4) A process for preparing a crystalline salt, preferably a hydrate, further preferred a dihydrate, of trans-5-chloro-2-methyl-2,3,3a,12b-tetrahydro-1H-dibenz[2,3:6,7]oxepino [4,5-c]pyrrole (Asenapine) with hydrochloric acid (HCl) according to any of items 1-3 comprising the steps of:
a) combining Asenapine free base with hydrochloric acid in a solvent or solvent mixture, optionally comprising water, optionally in the presence of seed crystals, preferably seed crystals of Asenapine maleate or Asenapine HCl, and
b) obtaining said crystalline Asenapine hydrochloride salt.

(5) The process of item 4, wherein the crystalline Asenapine HCl salt obtained in step (b) is selected from the group consisting of: Asenapine HCl dihydrate, a salt comprising Asenapine HCl dihydrate, Asenapine HCl anhydrous form I, a salt comprising Asenapine HCl anhydrous form I, Asenapine HCl anhydrous form II, and a salt comprising Asenapine HCl anhydrous form II. Preferably, the crystalline Asenapine HCl salt obtained in step (b) is selected from the group consisting of: Asenapine HCl dihydrate, Asenapine HCl anhydrous form I, and Asenapine HCl anhydrous form II, preferably Asenapine HCl dihydrate.

(6) The process of item 4 or 5, wherein the solvent or solvent mixture comprises one or more organic solvents from the group consisting of acetic acid $C_1$-$C_4$ alkyl esters, e.g. ethyl acetate; ketones, e.g. acetone, methylethylketone or methylisobutylketone; and nitriles, e.g. acetonitrile and additionally optionally comprises water.

(7) The process of any of items 4-6, wherein step (a) is carried out at a temperature of between 15° C. and 30° C. under stirring.

(8) A process for preparing crystalline Asenapine HCl salt hydrates, preferably Asenapine HCl dihydrate or a salt comprising Asenapine HCl dihydrate, according to item 1 comprising the steps of
a) preparing a suspension of crystalline Asenapine HCl anhydrous salt, preferably Asenapine HCl anhydrous form I or Asenapine HCl anhydrous form II in an aqueous solvent or solvent mixture, preferably in water, and optionally in the presence of seed crystals, and
b) isolating crystalline Asenapine HCl hydrates, preferably Asenapine HCl dihydrate, from the suspension.

(9) The process of item 8, wherein the suspension in step (a) is prepared and maintained at a temperature of between 15° C. and 30° C., preferably under stirring (e.g. 600 rpm), for a period of time sufficient to induce recrystallization, preferably for a period of time of between 2 hours and two days, further preferred for at least one day.

(10) A process for preparing a crystalline salt comprising Asenapine HCl anhydrous form II, preferably said salt consists of Asenapine HCl anhydrous form II, according to item 1 comprising the steps of:
a) preparing a suspension comprising crystalline Asenapine HCl dihydrate in an organic solvent or organic solvent mixture, preferably acetonitrile; or preparing a solution of Asenapine HCl in an organic solvent or an organic solvent mixture, preferably a mixture of isopropanol/tert-butyl methyl ether (TBME), which does not comprise water, and
b) isolating crystalline Asenapine HCl anhydrous form II from the suspension/solution.

(11) The process of item 10, wherein the suspension/solution in step (a) is prepared and maintained at a temperature of between 15° C. and 25° C. or 30° C., preferably under stirring (e.g. 600 rpm), for a period of time sufficient to induce recrystallization/crystallization, preferably for a period of time of between 2 hours and two weeks.

(12) Crystalline salt, in particular a crystalline hydrate, of Asenapine with hydrochloric acid according to any of items 1-3 or as prepared according to any of items 4-11 as medicament, preferably for the treatment of psychotic diseases or disorders, wherein the salt preferably is or comprises Asenapine HCl dihydrate.

(13) Pharmaceutical composition comprising one or more crystalline salts, in particular hydrates, of Asenapine with hydrochloric acid according to any of items 1-3 or crystalline salts of Asenapine with hydrochloric acid (HCl) prepared according to the process of any of items 4-11.

(14) Pharmaceutical dosage form comprising one or more crystalline salts, in particular hydrates, of Asenapine with hydrochloric acid (HCl) according to any of items 1-4 or crystalline salts of Asenapine with hydrochloric acid (HCl) prepared according to the process of any of items 4-11. Preferably, the dosage form comprises at least one pharmaceutically acceptable carrier or diluent.

(15) Pharmaceutical composition or dosage form of items 13 or 14, wherein at least 80 wt. % of Asenapine being present in said composition or dosage form is crystalline Asenapine HCl dihydrate, or crystalline Asenapine HCl anhydrous salt, preferably Asenapine HCl anhydrous form I or Asenapine HCl anhydrous form II.

DETAILED DESCRIPTION

Trans-5-chloro-2-methyl-2,3,3a,12b-tetrahydro-1H-dibenz[2,3:6,7]oxepino[4,5-c]pyrrole (Asenapine/Asenapine free base) has a structure according to Formula I:

The invention generally refers to crystalline Asenapine HCl salts. The crystalline salts according to the invention preferably have a solubility in water of at least 15 mg/ml, further preferred of at least 20 mg/ml, even further preferred of at least 24 mg/ml. A typical maximum solubility can e.g. be 40 mg/ml, 30 mg/ml or 25 mg/ml. The solubility of the salts is determined as described below.

Additionally preferred, the molar ratio of Asenapine to HCl is about 1:1. The ratio of Asenapine to HCl can also e.g. be 1:1.3 to 1.3:1. The ratio of Asenapine to HCl can be determined by elemental composition analysis (analysis of C, H, N, O, and Cl) using typical state of the art instrumentation and procedures.

Preferably, the crystalline salt comprises at least 80 wt. %, further preferred at least 90 wt. %, even further preferred at least 95 wt. %, of one or more, preferably one, selected from the group consisting of, (i) Asenapine HCl dihydrate, (ii) Asenapine HCl anhydrous form I, and (iii) Asenapine HCl anhydrous form II. The term "Asenapine HCl dihydrate" as used in the context of the invention refers to Asenapine HCl in the form of a dihydrate and having a crystal structure as described herein.

Within the meaning of the invention, the term "seed crystals" refers to that type of crystals that help produce the desired crystal form of Asenapine HCl salt. For example, if it is desired to produce crystalline Asenapine HCl dihydrate the seed crystals to be used can significantly enhance and improve the control over the recrystallization/crystallization process.

Surprisingly, it was found that crystalline Asenapine maleate salt can be used as seed crystals to prepare crystalline Asenapine hydrochloride. This very unusual seeding process then leads to the availability of hydrochloride salt seed crystals, which facilitate the production of larger quantities of Asenapine hydrochloride.

In accordance with the invention there is e.g. provided Asenapine HCl of Formula I ($H_2O$ molecules that are optionally present are not shown):

Water can be present in the HCl salts according to the invention in an amount of 0 to 4 molecules per Asenapine molecule, preferably 0 to 2 molecules per Asenapine molecule, also preferred between 2 and 4.

In one embodiment, a crystalline Asenapine HCl dihydrate is provided. The crystalline Asenapine hydrochloride dihydrate of the invention is characterized by X-ray powder diffraction reflections comprising peaks at two theta angles of about 4.6°±0.2°, 9.3°±0.2°, 14.0°±0.2°, 18.8°±0.2° and 24.9°±0.2°. The crystalline Asenapine hydrochloride dihydrate of the invention can be further characterized by a PXRD pattern substantially in accordance with FIG. 1. H-NMR spectroscopy shows protonated Asenapine and the elemental analysis indicates a 1:1 hydrochloride salt containing two equivalents of water.

Asenapine HCl dihydrate of the invention can absorb about 1.5% of additional water at 95% relative humidity at 25° C. and most of the water uptake occurs above 80% relative humidity as shown by dynamic vapor absorption. Therefore said Asenapine hydrochloride form is not, or only very slightly hygroscopic, thus very easy to handle and not critical to normal storage condition.

The aqueous solubility of the hydrochloride dihydrate of the invention was determined to be 24.2 mg/ml at 25° C. calculated as free base. The aqueous solubility was determined after 40 hours of suspension equilibration at 25° C. Thereafter, the suspension was filtered and the concentration in the liquid phase was determined by HPLC. The excellent solubility of the Asenapine hydrochloride dihydrate of the invention may render the salt to an excellent alternative to known salts of Asenapine, especially for a fast dissolving formulation.

The invention also relates to novel anhydrous crystal forms of Asenapine hydrochloride, designated as Form I and Form II.

Anhydrous form I of Asenapine hydrochloride is characterized by X-ray powder diffraction reflections comprising peaks at two theta angles of about 8.3°±0.2°, 9.0°±0.2°, 18.0°±0.2°, 24.3°±0.2° and 25.1°±0.2°. The crystalline Asenapine hydrochloride form I of the invention can be further characterized by a PXRD pattern substantially in accordance with FIG. 2. Thermogravimetric analysis of the anhydrous form I of Asenapine hydrochloride shows a small mass loss of about 0.7% up to a temperature of 180°.

Anhydrous form II of Asenapine hydrochloride is characterized by X-ray powder diffraction reflections comprising peaks at two theta angles of about 9.4°±0.2°, 17.1°±0.2°, 17.5°±0.2°, 18.9°±0.2° and 24.8°±0.2°. The crystalline hydrochloride anhydrous form II of the invention can be further characterized by a PXRD pattern substantially in accordance with FIG. 3.

Thermogravimetric analysis of the crystalline Asenapine HCl anhydrous form II shows only a mass loss of about 0.1% when heated at a heating rate of 10 K/min. Anhydrous form II of Asenapine hydrochloride is very easy to dry under very mild drying conditions, thus the salt has excellent properties with respect to drying.

The invention also refers to a process for preparing a crystalline salt, preferably a hydrate, further preferred a dihydrate, of trans-5-chloro-2-methyl-2,3,3a,12b-tetrahydro-1H-dibenz[2,3:6,7]oxepino[4,5-c]pyrrole (Asenapine) with hydrochloride (HCl) comprising the steps of:
a) combining Asenapine free base with hydrochloric acid in an organic solvent or organic solvent mixture optionally comprising water, optionally in the presence of seed crystals, preferably seed crystals of Asenapine maleate or Asenapine HCl, preferably crystals of the Asenapine HCl salt that is to be obtained in step (b), and
b) obtaining said crystalline Asenapine HCl salt.

Preferably, hydrochloric acid in step (a) is used as aqueous solution, preferably the concentration of the aqueous hydrochloric acid solution is 3-6M (molarity), preferably 6M. The hydrochloric acid can e.g. be used in an amount of between 1 and 3 equivalents, preferably in an amount of about one equivalent. As an alternative, it is also possible to treat a solution of Asenapine free base in an organic solvent with gaseous hydrochloric acid in order to preferably obtain anhydrous forms of Asenapine HCl. When hydrochloric acid is added in form of a gas then a slight excess, for instance about 1.05 to 2 equivalents, more preferably about 1.1 to 1.2 equivalents is recommended even if the process is carried out in a closed system.

As a further alternative, hydrochloric acid can be added in form of a solution in an organic solvent, typically at a concentration near the saturation limit at 25° C. For an organic solvent in which hydrochloric acid is well soluble typical concentrations may be from about 0.1 mol per liter to 2.0 mol per liter. If water is present in the reaction mixture when preparing anhydrous salts, the water is then preferably removed by distillation. The solvent mixture containing water will be distilled either to dryness or to about 10 to 30%, further non-aqueous solvent will be added and again distilled off to reach a sufficiently low level of water concentration. The solvent or solvent mixture preferably does not contain water or if water is present, then the acceptable level depends on the nature of the co-solvent. In general, the presence of water in the solvent mixture allows providing hydrates.

Additionally preferred, the crystalline Asenapine HCl salt obtained in step (b) is selected from the group consisting of: Asenapine HCl dihydrate, a salt comprising Asenapine HCl dihydrate, Asenapine HCl anhydrous form I, or a salt comprising Asenapine HCl anhydrous form I or Asenapine HCl anhydrous form II, or a salt comprising Asenapine HCl anhydrous form II.

Preferably, the solvent or solvent mixture is chosen to be suitable for completely dissolving Asenapine free base. Asenapine free base is well soluble in alcohols, e.g. ethanol, 1-propanol, 2-propanol, and 1-butanol, and in ketones, e.g., acetone, methyl ethyl ketone, and 2-pentanone, or in esters, e.g. ethyl acetate, isopropyl acetate, and butyl acetate, or in ethers such as THF or TBME. A typical concentration is about 0.1 to 5 mol per liter, preferably about 1 to 4 mol per liter, more preferably about 2 mol per liter.

Additionally preferred, the solvent or solvent mixture comprises one or more organic solvents from the group consisting of acetic acid $C_1$-$C_4$ alkyl esters, e.g. ethyl acetate; ketones, e.g. acetone, methylethylketone or methylisobutylketone; and nitriles, e.g. acetonitrile; and optionally comprises water. Water is preferably added in the form of an aqueous HCl solution.

The yields may be enhanced by addition of an antisolvent which is preferably selected from a set of pharmaceutically well acceptable solvents such as 2-propanol, and 1-butanol, methyl ethyl ketone, 2-pentanone, ethyl acetate, isopropyl acetate, butyl acetate, and TBME.

Additionally preferred, obtaining said crystalline Asenapine HCl salt in step (b) comprises isolation of said salt by filtration, washing the obtained salt and drying said salt.

Additionally preferred, step (a) is carried out at a temperature of between 15° C. and 30° C. under stirring (e.g. 600 rpm), for a period of time sufficient to induce crystallization, preferably of between 1 hour and two days.

Preferably, Asenapine HCl anhydrous form I or a salt comprising Asenapine HCl anhydrous form I, is prepared by using a solvent/solvent mixture comprising of alcohol, e.g. ethanol, 1-propanol, 2-propanol, and 1-butanol, a ketone, e.g., acetone, methyl ethyl ketone, and 2-pentanone, or an ester, e.g. ethyl acetate, isopropyl acetate, and butyl acetate, or an ether such as THF or TBME, or a nitrile, e.g. acetonitrile, or a mixture thereof. Water can also be present; however, the level of water should not exceed a certain level.

Crystalline Asenapine HCl dihydrate can be prepared by applying the steps of providing a solution of Asenapine base in an organic solvent by addition of hydrochloric acid in the presence of water. Suitable organic solvents include but are not limited to acetic acid $C_1$-$C_4$ alkyl esters, e.g. ethyl acetate; ketones, e.g. acetone, methylethylketone or methylisobutylketone or nitriles, e.g. acetonitrile. Preferably, Asenapine HCl dihydrate or a salt comprising Asenapine HCl dihydrate, is prepared by using ethyl acetate as solvent or a solvent mixture comprising ethyl acetate. Preferably an aqueous solution of hydrochloride acid is used in the crystallization of Asenapine hydrochloride dihydrate, e.g. an about 3 to 6 normal HCl.

Anhydrous form I of Asenapine may preferably be prepared by the above method by crystallizing from ethyl acetate or mixtures of ethyl acetate and acetonitrile, wherein the solvent/solvent mixture preferably does not comprise water.

Conveniently, Asenapine free base is combined with at least a stoichiometric amount of hydrochloric acid in ethyl acetate and optionally, if water is present in the reaction mixture, the water is then removed by distillation. However, the anhydrous form I can also be prepared by dissolving the free base in an organic solvent and add one equivalent of hydrochloric acid in form a solution in the same or in a different organic solvent. Alternatively, gaseous hydrochloric acid can be bubbled through the solution containing the free base.

Crystallization of anhydrous form I of Asenapine hydrochloride is then e.g. completed by suspending the residue in ethyl acetate or mixtures of ethyl acetate and acetonitrile, e.g. a mixture of ethyl acetate and acetonitrile of about 1:1 (v/v). Anhydrous form I of Asenapine hydrochloride may be isolated in conventional manner, e.g. by filtration and washed with a suitable organic solvent, e.g. methyl tert. butyl ether followed by drying.

Salts comprising or consisting of Asenapine HCl anhydrous form II are preferably prepared in acetonitrile, further preferred in a mixture of isopropanol/tert-butyl methyl ether (TBME), wherein the solvent/solvent mixture preferably does not comprise water.

Another embodiment relates to a process for preparing crystalline Asenapine HCl salt hydrates, preferably Asenapine HCl dihydrate or a salt comprising Asenapine HCl dihydrate comprising the steps of
a) preparing a suspension of crystalline Asenapine HCl anhydrous salt, preferably Asenapine HCl anhydrous form I or Asenapine HCl anhydrous form II in an aqueous solvent or solvent mixture, preferably in water, and optionally in the presence of seed crystals, and
b) isolating crystalline Asenapine HCl hydrates, preferably Asenapine HCl dihydrate, from the suspension.

Additionally preferred, the suspension in step (a) is prepared and maintained at a temperature of between 15° C. and 50° C., preferably under stirring (e.g. 600 rpm), for a period of time sufficient to induce recrystallization. A sufficient time is between 1 hour and five days. The suspension is preferably stirred for a period of time of between 2 hours and two days, further preferred is a stirring time of 2 to 24 hours.

Preferably, crystalline Asenapine hydrochloride dihydrate of the invention may be prepared by suspending anhydrous form I of Asenapine hydrochloride or anhydrous form II of Asenapine hydrochloride in water for a sufficient time to induce crystallization of the dihydrate.

Time and temperature in the transformation step is not critical. The anhydrous forms I and II of Asenapine hydrochloride are preferably suspended in water and the suspension is allowed to stand for about 1 hour or less up to e.g. to 48 hours at ambient temperature optionally in the presence of seeds. The suspension can then be filtered and the crystalline Asenapine hydrochloride dihydrate can then be isolated followed optionally by drying.

Seeds of the Asenapine hydrochloride dihydrate may e.g. be prepared by combining Asenapine free base in ethylacetate with a solution of aqueous hydrochloric acid and seeds of Asenapine maleate according to EP 1917267. The preparation of seeds is exemplified in Example 1.

Another embodiment relates to a process for preparing a crystalline salt comprising Asenapine HCl anhydrous form II, preferably said salt consists of Asenapine HCl anhydrous form II comprising the steps of:
a) preparing a suspension comprising crystalline Asenapine HCl dihydrate or preparing a solution of Asenapine HCl, in an organic solvent, preferably acetonitrile, or an organic solvent mixture, preferably a mixture of isopropanol/tert-butyl methyl ether (TBME), which does not comprise water, and
b) isolating crystalline Asenapine HCl anhydrous form II from the suspension/solution.

When preparing Asenapine HCl anhydrous form, it is preferred that water—if present in the reaction mixture—is removed e.g. by distillation.

Additionally preferred, the suspension/solution in step (a) is prepared and maintained at a temperature of between 15° C. and 30° C., preferably between 20° C. and 25° C., preferably under stirring (e.g. 600 rpm), for a period of time sufficient to induce recrystallization/crystallization, preferably for a period of time of between 2 hours and two weeks.

Preferably, when preparing Asenapine HCl anhydrous form II from Asenapine HCl dihydrate, the suspension in step (a) is prepared and maintained at a temperature of between 15° C. and 30° C., preferably under stirring (e.g. 600 rpm). The suspension is preferably stirred for a period of time sufficient to induce crystallization, preferably for a period of time of between one day and two weeks, further preferred for at least one week. The product can be recovered by filtration.

Preferably, when preparing Asenapine HCl anhydrous form II from a solution of Asenapine HCl (by crystallization), the solution in step (a) is prepared and maintained at a temperature of between 15° C. and 25° C. or 30° C., preferably under stirring (e.g. 600 rpm). The solution is preferably stirred for a period of time of between one day and two weeks, further preferred for at least four days. The product can be recovered by filtration.

Anhydrous form II of Asenapine hydrochloride is preferably prepared by crystallization from a solution of Asenapine HCl in a solvent mixture of isopropanol and methyl-tert. butyl ether. Any kind of Asenapine hydrochloride is suitable as starting material, e.g. Asenapine hydrochloride anhydrous form I or Asenapine hydrochloride dihydrate or a solution of Asenapine base and hydrochloric acid. Suitable mixtures of isopropanol to methyl tert. butyl ether include but are not limited to mixtures of about 1:1 (v/v) to 1:4 (v/v) isopropanol to methyl tert. butyl ether.

Alternatively anhydrous form II of Asenapine is accessible by slurrying Asenapine dihydrate in acetonitrile for a time sufficient for the conversion of the dihydrate to the anhydrous form II, e.g. by slurring the crystalline dihydrate of the invention in acetonitrile for about 7 days at room temperature.

Anhydrous form II of Asenapine may be isolated by conventional methods, e.g. filtration and drying.

The invention also refers to crystalline salts of Asenapine obtainable or obtained according to the processes as described above.

The invention also refers to a crystalline salt, in particular hydrate, of Asenapine with hydrochloride (HCl) as described herein as medicament, preferably for the treatment of psychotic diseases or disorders, wherein the salt preferably is or comprises Asenapine HCl dihydrate.

Another embodiment refers to a pharmaceutical composition comprising one or more crystalline salts, in particular hydrates, of Asenapine with hydrochloride (HCl) according the invention.

Another embodiment refers to a pharmaceutical dosage form comprising one or more crystalline salts, in particular hydrates, of Asenapine with hydrochloride (HCl) according to the invention. Preferably, the dosage form comprises at least one pharmaceutically acceptable carrier or diluent.

Additionally preferred, at least 80 wt. % of Asenapine being present in said composition or dosage form is crystalline Asenapine HCl dihydrate or crystalline Asenapine HCl anhydrous salt, preferably Asenapine HCl anhydrous form I or Asenapine HCl anhydrous form II. Further preferred, at least 80 wt. %, further preferred at least 90 wt. % and most preferred at least 95 wt. % of Asenapine being present in the composition or dosage form is Asenapine HCl dihydrate.

The crystalline Asenapine hydrochloride dihydrate of the invention of the invention may be formulated as disclosed for example in Example 16 of WO 2006/106135 by mixing the novel crystalline salt into a gelatin/mannitol/water mixture and freeze drying, preferably after dosing into pre-formed pockets.

Powder X-ray diffraction: PXRD was carried out with a Bruker D8 Advance powder X-ray diffractometer using $Cu_{K\alpha}$ radiation in reflection (Bragg-Brenatno) geometry. $2\theta$ values usually are accurate within an error of ±0.1-0.2°. The samples were generally prepared without any special treatment other than the application of slight pressure to get a flat surface. Two different Silicon single crystal sample holder types were used: a) a standard holder with 0.1 mm in depth, and b) a 0.5 mm depth sample holder with 12 mm cavity diameter. Normally samples were measured uncovered. The tube voltage was 40 kV and current was 40 mA. The PXRD diffractometer is equipped with a LynxEye detector. A variable divergence slight was used with a 3° window. The step size was 0.02° $2\theta$ with a step time of 37 seconds. The samples were rotated at 0.5 rps during the measurement.

DSC:

Differential scanning calorimetry was carried out with a Perkin Elmer DSC-7 instrument (closed gold sample pan or gold-plated steel sample pan, heating rates 10 and 20 K/min).

TG-FTIR:

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

Solvents:

Generally, Merck or Fluka analytical grade solvents were used.

HPLC Method:

An HPLC instrument from TSP (UV3000, AS3000, P4000, SCM1000 using software version 4.1) was used in combination with a column from Waters (XTerra MS 018, 4.6×100 mm, 5 μm (CC01A)). The mobile phase A was H2O/ACN 95:5 with 0.1% TFA, and mobile phase B was H2O/ACN 5:95 with 0.1% TFA. The reference concentration was 0.09 mg/mL. The Asenapine peak appeared at a retention time.

4.0-4.1 min. The method was isocratic with 70% mobile phase A and 30% mobile phase B at 0 min and after 10 min at a flow of 1.0 mL/min. The injection volume was 10 µL and the detection wavelength 202 nm.

Determining Solubility of Asenapine HCl Salts:

The aqueous solubility of Asenapine salts is determined in water after 48 hours of suspension equilibration at 25° C. 200 mg of Asenapine hydrochloride is suspended in 1.5 ml of bidistilled water and the resulting suspension is placed on a laboratory shaker at 500 rpm. Thereafter, the suspension is filtered and the concentration in the liquid phase was determined by HPLC as described above.

REFERENCE EXAMPLE 6.43 g of Asenapine maleate were added with stirring to a mixture of 40 ml of 1 M NaOH and 320 ml of methyl-tert. butyl ether (TBME). The mixture was stirred for 10 min and the layers were separated. The aqueous layer was extracted with 320 ml of methyl-tert. butyl ether. The combined organic layers were extracted with 150 ml of water.

The organic layer was dried with 13.6 g of sodium sulfate. The suspension was filtered and the solution was concentrated in vacuo at about 40° C. and 20 ml.

Yield:

3.77 g of Asenapine free base (as an oil)

Example 1

Preparation of Asenapine Hydrochloride Dihydrate Seed Crystals 125 mg Asenapine free base (~0.42 mmol) was dissolved in 4.0 ml ethyl acetate and to this solution one equivalent of hydrochloric acid (75 µl) was added in form of a 6M aqueous solution (Riedel-de Haen #35277). Upon addition of the acid a slightly turbid solution was obtained to which about one mg of Asenapine maleate according to EP 191726781 was added as seed crystals. After about 45 minutes the suspension was filtered and the obtained solid dried under vacuum at room temperature, then investigated by H-NMR, powder X-ray diffraction, TG-FTIR, and elemental composition analysis. H-NMR spectroscopy showed protonated Asenapine and the elemental analysis indicated a 1:1 hydrochloride salt containing two equivalents of water. The result from the elemental composition analysis is shown in Table 2. Powder X-ray diffraction confirmed that the salt was crystalline and it showed a PXRD pattern as depicted in FIG. 1 with the most important peaks as provided in Table 1. TG-FTIR indicated a mass loss of about 3% which was attributable to the presence of water.

TABLE 1

PXRD peak table for the crystalline Asenapine hydrochloride dihydrate

| Angle 2θ | d-spacings [Å] | qualitative relative intensity |
|---|---|---|
| 4.6 | 19.00 | M |
| 9.3 | 9.48 | S |
| 14.0 | 6.31 | S |
| 14.2 | 6.24 | W |
| 18.2 | 4.88 | W |
| 18.8 | 4.73 | Vs |
| 20.1 | 4.42 | W |
| 24.0 | 3.70 | W |
| 24.6 | 3.62 | W |
| 24.9 | 3.58 | M |
| 25.3 | 3.52 | M |

TABLE 1-continued

PXRD peak table for the crystalline Asenapine hydrochloride dihydrate

| Angle 2θ | d-spacings [Å] | qualitative relative intensity |
|---|---|---|
| 25.6 | 3.48 | W |
| 27.7 | 3.22 | W |
| 38.1 | 2.36 | W |

TABLE 2

Result of the elemental composition analysis for crystalline Asenapine hydrochloride dihydrate

| Element | % Found | % Expected |
|---|---|---|
| C | 57.4 | 57.0 |
| H | 5.9 | 5.9 |
| N | 4.1 | 3.9 |
| O | 12.7 | 13.4 |
| Cl | 20.0 | 19.8 |

Example 2

Preparation of Anhydrous Asenapine Hydrochloride Form I 303 mg of Asenapine free base was dissolved in 4.0 ml acetonitrile and to this solution was added 170 µl hydrochloric acid in form of a 6M aqueous solution (Riedel-de Haen #35277). The solution was seeded with about 1 mg of crystalline Asenapine hydrochloride according to Example 1; however, the seed crystals dissolved. Addition of 3.0 ml ethyl acetate did not lead to a suspension and therefore, the solvents were evaporated under nitrogen. To the white solid residue 1.0 ml acetonitrile and 1.0 ml ethyl acetate was added and the resulting suspension was stirred at room temperature overnight. Then the suspension was filtered, the obtained solid washed with 5 ml TBME and solid dried in air at room temperature. The obtained sample was characterized by powder X-ray diffraction, H-NMR, TG-FTIR, DSC, and light microscopy. A PXRD pattern as shown in FIG. 2 with the most important peaks as indicated in Table 3 was found. H-NMR spectroscopy showed protonated Asenapine. Even after a very short drying time at room temperature the TG analysis revealed a mass loss of only about 0.5% upon heating to 150° C. at a rate of 10 K/min. This shows that the crystalline form of the salt has excellent properties with respect to drying.

TABLE 3

PXRD peak table for crystalline Asenapine hydrochloride anhydrous form I

| Angle 2θ | d-spacings [Å] | qualitative relative intensity |
|---|---|---|
| 4.5 | 19.63 | w |
| 6.0 | 14.78 | w |
| 8.3 | 10.60 | vs |
| 9.0 | 9.87 | vs |
| 10.8 | 8.21 | s |
| 13.6 | 6.51 | m |
| 16.6 | 5.34 | m |
| 16.8 | 5.29 | s |
| 17.1 | 5.18 | s |
| 17.7 | 4.99 | m |
| 18.0 | 4.91 | vs |
| 19.1 | 4.64 | s |

TABLE 3-continued

PXRD peak table for crystalline Asenapine hydrochloride anhydrous form I

| Angle 2θ | d-spacings [Å] | qualitative relative intensity |
|---|---|---|
| 21.6 | 4.11 | s |
| 22.8 | 3.90 | m |
| 23.7 | 3.76 | s |
| 24.3 | 3.65 | vs |
| 24.6 | 3.62 | s |
| 25.1 | 3.54 | vs |
| 26.3 | 3.38 | s |
| 26.5 | 3.36 | s |
| 26.9 | 3.31 | s |
| 27.2 | 3.27 | s |
| 27.5 | 3.25 | m |
| 28.5 | 3.13 | s |
| 28.8 | 3.09 | s |
| 29.2 | 3.05 | m |
| 30.4 | 2.93 | s |
| 32.4 | 2.76 | s |
| 34.5 | 2.60 | m |
| 35.7 | 2.51 | m |
| 38.2 | 2.36 | m |

Example 3

Conversion of Crystalline Anhydrous Asenapine Hydrochloride Form I into Crystalline Asenapine Hydrochloride Dihydrate and Solubility Determination 97 mg of hydrochloride salt form I according to Example 2 was suspended in 2.0 ml water and the vial with the suspension was placed on a standard laboratory shaker (Eppendorf) at 25° C. and 600 rpm for two days. After two days of equilibration the suspension was filtered and the recovered solid investigated by PXRD which confirmed the presence of form I according to Example 1 with a PXRD pattern as shown in FIG. 1. The aqueous solubility was determined by measuring the concentration of Asenapine in the filtered solution by HPLC, which was found to be 24.2 mg/ml at a pH of 4.0.

Example 4

Preparation of Asenapine Hydrochloride Dihydrate 504 mg Asenapine free base was dissolved in 5.0 ml ethyl acetate and to this solution was added 282 μl HCl in form of a 6M aqueous solution (Riedel-de Haen #35277). The obtained suspension was stirred at room temperature for one day before the solid product was separated by filtration. Drying was performed at room temperature under vacuum overnight and about 406 mg of crystalline form I was obtained as the PXRD pattern was identical with the crystalline form according to Example 1.

Example 5

Preparation of Asenapine Hydrochloride Anhydrous Form II

To 105 mg of Asenapine hydrochloride dihydrate was added 2.0 ml acetonitrile and the obtained suspension was stirred for one week at room temperature, then filtered and the solid product dried in air at room temperature. The obtained sample was characterized by powder X-ray diffraction and a PXRD pattern as depicted in FIG. 3 with the most important peaks as listed in Table 4 was obtained. The H-NMR spectrum confirmed the presence of protonated Asenapine.

TABLE 4

PXRD peak table for the Asenapine hydrochloride anhydrous form II

| Angle 2θ | d-spacings [Å] | qualitative relative intensity |
|---|---|---|
| 8.3 | 10.68 | w |
| 9.4 | 9.39 | vs |
| 12.7 | 6.97 | w |
| 14.8 | 5.97 | m |
| 15.5 | 5.71 | m |
| 17.1 | 5.18 | s |
| 17.5 | 5.07 | s |
| 18.0 | 4.92 | m |
| 18.6 | 4.76 | m |
| 18.9 | 4.69 | s |
| 21.1 | 4.21 | m |
| 21.2 | 4.19 | m |
| 21.7 | 4.10 | m |
| 24.8 | 3.59 | s |
| 26.0 | 3.42 | m |
| 26.5 | 3.36 | m |
| 26.9 | 3.31 | m |
| 27.1 | 3.29 | m |
| 27.9 | 3.19 | m |

Example 6

Preparation of Asenapine Hydrochloride Salt Anhydrous Form II

To 65 mg of Asenapine hydrochloride form I was added 2.0 ml isopropanol and 2.0 ml TBME. A clear solution was obtained from which the solvents were evaporated to dryness. Thereafter, 1.0 ml isopropanol and 2.0 ml TBME were added and the mixture sonicated for about one minute. After stirring at room temperature for four days the obtained suspension was filtered and the solid product dried in air at room temperature. The obtained sample was characterized by powder X-ray diffraction and TG-FTIR. The TG mass loss upon heating to 200° C. at a heating rate of 10 K/min was about 0.1% which indicates that even after very mild drying conditions a crystalline form essentially free of residual solvents was obtained. This shows that the crystalline form of the salt has excellent properties with respect to drying.

A powder X-ray diffraction pattern as shown in FIG. 3 with the most important peaks as listed in Table 4 was obtained.

CITED DOCUMENTS

WO 98/54186
EP 0569096
WO 2006/106135
Funke et. al. (Arzneim.-Forsch./Drug Res. 40, 1999, 536-539)
WO2009/135091
Peter van Hoof et al. (Amorphous Pharmaceutical Materials, September 2009)
US 2008/0306133 A1.

The invention claimed is:
1. A crystalline salt, which is a hydrate of trans-5-chloro-2-methyl-2,3,3a,12b-tetrahydro-1H-dibenz[2,3:6,7]oxepino[4,5-c]pyrrole (Asenapine) with hydrochloride (HCl).
2. The crystalline salt of claim 1, wherein the solubility of said salt in water is at least 15 mg/ml, calculated as free base equivalent, and/or wherein the molar ratio of Asenapine to HCl in said salt is between 1:1.3 to 1.3:1.

3. The crystalline salt of claim 1 comprising Asenapine HCl dihydrate, wherein the Asenapine HCl dihydrate is characterized by X-ray powder diffraction reflections (Cu Kα radiation) comprising peaks at about 18.8°±0 2° 9.3°±0.2°, 14.00±0.2°, 24.9°±0.2° and 4.6°±0.2° degrees two-theta.

4. A process for preparing a crystalline salt, which is a hydrate, of trans-5-chloro-2-methyl-2,3,3a,12b-tetrahydro-1H-dibenz[2,3:6,7]oxepino[4,5-c]pyrrole (Asenapine) with hydrochloride (HCl) according to claim 1 comprising the steps of:
  a) combining Asenapine free base with hydrochloric acid in an organic solvent or organic solvent mixture, optionally comprising water, and
  b) obtaining said crystalline Asenapine HCl salt.

5. The process of claim 4, wherein the crystalline Asenapine HCl salt obtained in step (b) is selected from the group consisting of: Asenapine HCl dihydrate, a salt comprising Asenapine HCl dihydrate, Asenapine HCl anhydrous form I, a salt comprising Asenapine HCl anhydrous form I, Asenapine HCl anhydrous form II, and a salt comprising Asenapine HCl anhydrous form II.

6. The process of claim 4, wherein the solvent or solvent mixture comprises one or more organic solvents from the group consisting of acetic acid $C_1$-$C_4$ alkyl esters, e.g. ethyl acetate; ketones, methylethylketone or methylisobutylketone; and nitrites.

7. The process of claim 4, wherein step (a) is carried out at a temperature of between 15° C. and 30° C. under stirring.

8. A process for preparing crystalline Asenapine HCl salt hydrates according to claim 1, comprising the steps of:
  a) preparing a suspension of crystalline Asenapine HCl anhydrous salt, which is either Asenapine HCl anhydrous form I or Asenapine HCl anhydrous form II, in an aqueous solvent or solvent mixture, and optionally in the presence of seed crystals, and
  b) isolating crystalline Asenapine HCl hydrates from the suspension.

9. The process of claim 8, wherein the suspension in step (a) is prepared and maintained at a temperature of between 15° C. and 30° C., under stirring, for a period of time sufficient to induce crystallization.

10. A process for preparing a crystalline salt comprising Asenapine HCl anhydrous form II, according to claim 1 comprising the steps of:
  a) preparing a suspension comprising crystalline Asenapine HCl dihydrate in an organic solvent or organic solvent mixture, or preparing a solution of Asenapine HCl in an organic solvent or organic solvent mixture, wherein the suspension/solution does not comprise water, and
  b) isolating crystalline Asenapine HCl anhydrous form II from the suspension/solution.

11. The process of claim 10, wherein the suspension/solution in step (a) is prepared and maintained at a temperature of between 15° C. and 30° C., under stirring, for a period of time sufficient to induce recrystallization/crystallization.

12. A pharmaceutical composition comprising one or more crystalline salts according to claim 1 and pharmaceutically acceptable excipients.

13. A pharmaceutical composition according to claim 12, wherein at least 80 wt. % of Asenapine being present in said composition is Asenapine HCl dihydrate.

* * * * *